United States Patent
Cox et al.

(10) Patent No.: US 9,625,584 B1
(45) Date of Patent: Apr. 18, 2017

(54) SYSTEMS AND METHODS FOR A LINEARLY FILLED NUCLEAR IMAGING PHANTOM

(71) Applicant: Wisconsin Alumni Research Foundation, Madison, WI (US)

(72) Inventors: Benjamin Cox, Madison, WI (US); Mohammed Farhoud, Los Angeles, CA (US); Stephen Graves, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 12 days.

(21) Appl. No.: 14/947,579

(22) Filed: Nov. 20, 2015

(51) Int. Cl.
G01T 1/164 (2006.01)
G01D 18/00 (2006.01)
A61B 6/00 (2006.01)
A61B 17/00 (2006.01)

(52) U.S. Cl.
CPC ............ *G01T 1/1648* (2013.01); *A61B 6/583* (2013.01); *G01D 18/00* (2013.01); *A61B 2017/00707* (2013.01)

(58) Field of Classification Search
CPC A61B 2017/00716; A61B 2017/00725; A61B 6/582; A61B 6/583; A61B 6/587; G01D 18/00; G01N 21/278; G01R 33/58; G01T 1/1648
See application file for complete search history.

(56) References Cited

U.S. PATENT DOCUMENTS

| 4,419,577 | A | * | 12/1983 | Guth | G01T 1/1648 250/252.1 |
|---|---|---|---|---|---|
| 4,499,375 | A | * | 2/1985 | Jaszczak | G01D 18/00 250/252.1 |
| 4,692,704 | A | * | 9/1987 | Gray | G01R 33/58 324/300 |
| 6,205,871 | B1 | * | 3/2001 | Saloner | G09B 23/28 430/325 |
| 6,744,039 | B1 | | 6/2004 | DiFilippo | |
| 6,821,898 | B2 | | 11/2004 | Beebe et al. | |
| 7,165,566 | B2 | | 1/2007 | Beebe | |
| 8,608,484 | B2 | * | 12/2013 | Kalafut | G09B 23/32 434/262 |
| 8,666,133 | B2 | * | 3/2014 | Vermandel | G01N 29/0654 378/207 |
| 2002/0178845 | A1 | * | 12/2002 | Jaszczak | G09B 23/28 73/866.4 |
| 2003/0086535 | A1 | * | 5/2003 | Teppaz | A61B 6/583 378/207 |

(Continued)

OTHER PUBLICATIONS

Alva-Sanchez, Energy Calibration of Individual Crystals in a LYSO Pixelated Array for MicroPET Detection Modules Using Voronoi Diagrams, Nuclear Instruments and Methods in Physics Research A, 2008, 596:384-389.

(Continued)

*Primary Examiner* — Mark R Gaworecki
(74) *Attorney, Agent, or Firm* — Quarles & Brady, LLP

(57) ABSTRACT

A phantom for a nuclear imaging system is provided. In particular, systems and method are provided for a phantom including a pattern plate having a plurality of passages and a plurality of channels sequentially interconnecting each of the plurality of cylindrical cavities.

20 Claims, 6 Drawing Sheets

(56) References Cited

U.S. PATENT DOCUMENTS

| | | | | |
|---|---|---|---|---|
| 2009/0098521 | A1* | 4/2009 | Kuo | G09B 23/30 434/267 |
| 2009/0316972 | A1* | 12/2009 | Borenstein | A61B 6/583 382/131 |
| 2010/0080339 | A1* | 4/2010 | Austin | G06T 11/006 378/4 |
| 2010/0261811 | A1* | 10/2010 | Thomas | G01N 21/278 524/1 |
| 2011/0293074 | A1* | 12/2011 | Coolens | G09B 23/303 378/207 |

OTHER PUBLICATIONS

Graves, et al., Novel Preparation Methods of 52Mn for ImmunoPET Imaging, Bioconjugate Chem., 2015, 26:2118-2124.

* cited by examiner

SYSTEMS AND METHODS FOR A LINEARLY FILLED NUCLEAR IMAGING PHANTOM

CROSS-REFERENCES TO RELATED APPLICATIONS

Not Applicable.

STATEMENT REGARDING FEDERALLY SPONSORED RESEARCH

Not Applicable.

BACKGROUND

The disclosure relates generally to quality assurance (QA) for nuclear imaging systems and, more specifically, to systems and methods for a linearly filled nuclear imaging phantom.

Nuclear imaging systems, for example single photon emission computed tomography (SPECT) systems and positron emission tomography (PET) systems, commonly use phantoms for quantifying imaging characteristics and for QA. Regular QA is essential to ensure that the images acquired by the nuclear imaging systems are of proper image quality and accuracy.

Typically, the phantoms are filled with a positron emitting radioisotope in fluid (e.g., water) to define a specific geometry which is then scanned by the nuclear imaging system. Various phantom geometries are used to measure specific imaging characteristics (e.g., spatial resolution, sensitivity, attenuation, etc.). One such phantom that is used in clinical and research applications to test the resolution capability of a nuclear imaging system is a Derenzo style phantom. Derenzo style phantoms include six hole patterns which each define a triangular shape and combine to form a hexagonal shape. The same size, or diameter, holes are used within an individual hole pattern, but the size of the holes change from pattern to pattern around the hexagonal shape. Each hole within an individual hole pattern is arranged at a distance that is twice that hole's diameter from adjacent holes.

BRIEF SUMMARY

The present disclosure provides a phantom for a nuclear imaging system that is linearly filled with fluid. In particular, the present disclosure provides systems and methods for a phantom having a plurality of passages that are configured to be linearly filled with fluid.

In one aspect, the present disclosure provides a phantom for a nuclear imaging system. The phantom includes a pattern plate including a plurality of passages extending through the pattern plate from a first opening on a first side of the pattern plate to a second opening on an opposing second side of the pattern plate. The phantom further includes a plurality of channels arranged on the first side of the pattern plate and the second side of the pattern plate to sequentially interconnect each of the plurality of passages thereby forming a continuous flow path from an inlet passage of the pattern plate to an outlet passage of the pattern plate.

In another aspect, the present disclosure provides a phantom for a nuclear imaging system. The phantom includes a pattern plate including a plurality of passages each extending through the pattern plate from a first opening on a first side of the pattern plate to a second opening on an opposing second side of the pattern plate. The phantom further includes a plurality of continuous fluid flow paths arranged on the first side of the pattern plate and the second side of the pattern plate to sequentially interconnect each of the plurality of passages from an inlet passage of the pattern plate to an outlet passage of the pattern plate.

In yet another aspect, the present disclosure provides a method of determining an imaging characteristic of a nuclear imaging system using a phantom fillable with a radioisotope doped fluid. The phantom includes a pattern plate and a continuous fluid flow path. The pattern plate includes a plurality of passages arranged in a calibration pattern. The plurality of passages includes an inlet passage and an outlet passage. The continuous fluid flow path sequentially interconnects each of the plurality of passages from the inlet passage to the outlet passage. The method includes furnishing the radioisotope doped fluid to the inlet passage of the pattern plate, filling the plurality of passages in the pattern plate, via the continuous fluid flow path, with a pre-determined volume of the radioisotope doped fluid. The method further includes upon filling the plurality of passages with the pre-determined volume of radioisotope doped fluid, imaging, with the nuclear imaging system, a cross-section of the pattern plate which defines the calibration pattern, and upon imaging the cross-section of the pattern plate which defines the calibration pattern, determining the imaging characteristic of the nuclear imaging system.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

DETAILED DESCRIPTION

Currently, nuclear imaging phantoms (e.g., Derenzo style phantoms) include a cylinder having a hole pattern drilled therein and a chamber for receiving the cylinder. The cylinder is placed within the chamber, and the chamber is then filled with a positron emitting radioisotope (e.g., $^{52}$Mn, $^{64}$Cu, $^{76}$Br, $^{124}$I) in fluid (e.g., water) in an attempt to fill the hole pattern in the cylinder so the phantom can be imaged using a nuclear imaging system.

However, several problems exist with these current phantoms designs. For example, when the hole patterns are submerged in the fluid, the smaller holes often do not fill because of the surface tension of the fluid. Incomplete filling of the holes in the phantom leads to air bubbles in the hole pattern thereby making it difficult or impossible to effectively image the phantom. Additionally, the entire chamber of the phantom must be filled with the radioisotope doped fluid. A volume of fluid required to fill the hole pattern is significantly less than a volume of fluid required to fill the chamber. Therefore, the current phantom designs do not utilize (i.e., waste) a significant volume of the radioisotope doped fluid in the chamber. It is well known in the art that the radioisotopes put into these phantoms represent a significant cost to research and clinical institutions and, thus, wasted volume is directly proportional to additional cost. Furthermore, the current phantom designs require a significant dosage (i.e., concentration) of the radioisotope to accompany the large volume of fluid required to fill the chamber.

Due to the deficiencies in current nuclear imaging phantom designs, it would be desirable to have a nuclear imaging phantom that is linearly filled with fluid to ensure the hole pattern of the phantom is completely filled with fluid. This would also enable the phantom to utilize only a volume of radioisotope doped fluid necessary to fill the hole pattern. That is, the phantom would not require any radioisotope doped fluid to be wasted, and enable the phantom to utilize a reduced dosage (i.e. concentration) of the radioisotope in the fluid.

Figure 1:
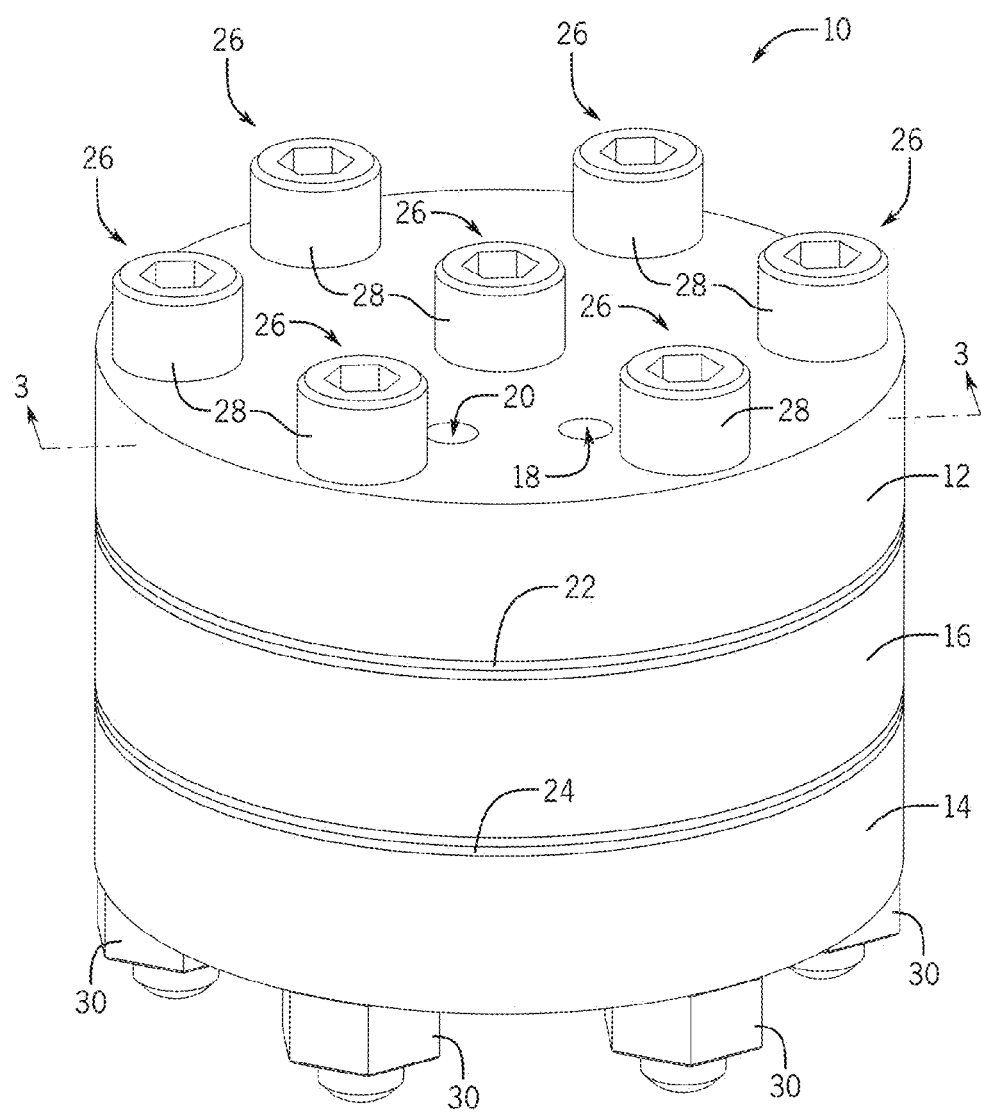
FIG. 1 shows a perspective view of a phantom for a nuclear imaging system according to one embodiment of the present disclosure.

FIG. 1 shows one non-limiting example of a phantom 10 for a nuclear imaging system (e.g., PET, SPECT, etc.) according to the present disclosure. The phantom 10 includes a first closing plate 12, a second closing plate 14, and a pattern plate 16 arranged between the first closing plate 12 and the second closing plate 14. The first closing plate 12, the second closing plate 14, and the pattern plate 16 each define a generally cylindrical shape, and each are fabricated from a material which does not interfere with the nuclear imaging system (e.g., a non-metallic material such as plastic or glass). In other non-limiting examples, the first closing plate 12, the second closing plate 14, and/or the pattern plate 16 may define an alternative shape, for example a rectangular or elliptical shape, as desired.

The first closing plate 12 includes an inlet 18 and an outlet 20. The inlet 18 is in fluid communication with the outlet 18 via a flow path in the pattern plate 16, as will be described in detail below. In some non-limiting examples, the inlet 18 and the outlet 20 can be coupled to a fitting (e.g., a Luer lock fitting) to enable the inlet 18 and the outlet 20 to be coupled to a Leur lock syringe. In other non-limiting examples, the inlet 18 and the outlet 20 may be coupled to a tube or a syringe pump device. In any case, the inlet 18 is configured to receive a fluid which is then furnished to the outlet 20 via the flow path in the pattern plate 16. It should be known that the mechanism used to furnish the fluid from the inlet 18 to the outlet 20 it not meant to be limiting in any way. In other non-limiting examples, one of the inlet 18 and the outlet 20 may be arranged on the first closing plate 12 and the other may be arranged on the second closing plate 14.

The phantom 10 includes a first gasket 22 arranged between the first closing plate 12 and the pattern plate 16, and a second gasket 24 arranged between the second closing plate 14 and the pattern plate 16. The first gasket 22 and the second gasket 24 each define a generally cylindrical shape, and are fabricated from a material which does not interfere with the nuclear imaging system (e.g., a non-metallic material such as silicon). The first gasket 22 is configured to provide a seal between the first closing plate 12 the pattern plate 16 to prevent fluid from leaking from the phantom 10 when fluid is furnished from the inlet 18 to the outlet 20. Similarly, the second gasket 24 is configured to provide a seal between the second closing plate 14 and the pattern plate 16 to prevent fluid from leaking from the phantom 10 when fluid is furnished from the inlet 18 to the outlet 20.

A plurality of fastening elements 26 fasten the pattern plate 16 between the first closing plate 12 and the second closing plate 14, and compress the first gasket 22 and the second gasket 24. The fastening elements 26 are fabricated from a material which does not interfere with the nuclear imaging system (e.g., a non-metallic material such as plastic, glass, or glass-filled nylon). The illustrated phantom 10 includes seven fastening elements 26 each in the form of a bolt 28 and a nut 30. It should be known that the number of fastening elements 26 is not meant to be limiting in any way. That is, the phantom 10 may include more or less than seven fastening elements 26 as long as the pattern plate 16, the first gasket 22 and the second gasket 24 are sufficiently and uniformly compressed between the first closing plate 12 and the second closing plate 14. In other non-limiting examples, the fastening elements 26 may be in the form of a clamping device or another compressive mechanism known in the art.

Figure 2:
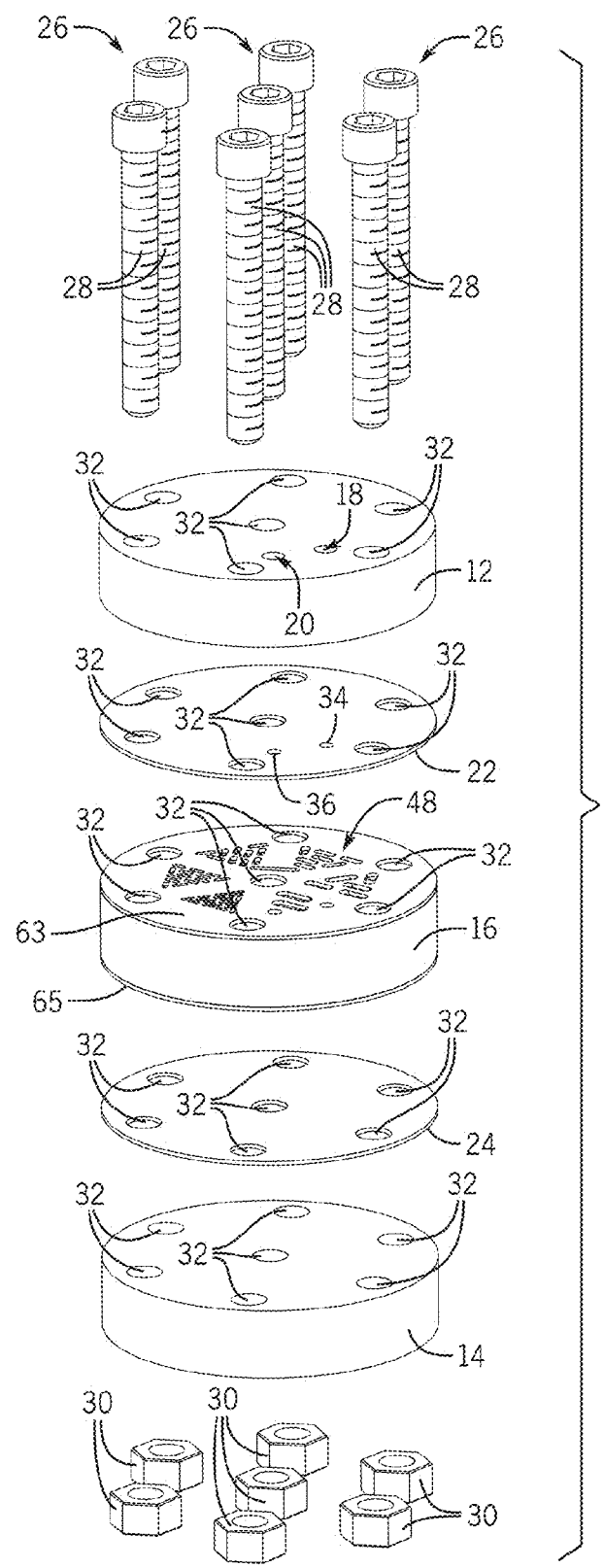
FIG. 2 shows an exploded view of the phantom of FIG. 1.

Turning to FIG. 2, each of the first closing plate 12, the second closing plate 14, the pattern plate 16, the first gasket 22, and the second gasket 24 include a plurality of fastener apertures 32. Each of the fastener apertures 32 in the first closing plate 12 are axially aligned with a corresponding fastener aperture 32 in the second closing plate 14, the pattern plate 16, the first gasket 22, and the second gasket 24. In this way, the fastener apertures 32 combine to form through holes extending from the first closing plate 12 through the second closing plate 14 each for receiving a corresponding one of the bolts 28.

Figure 3:
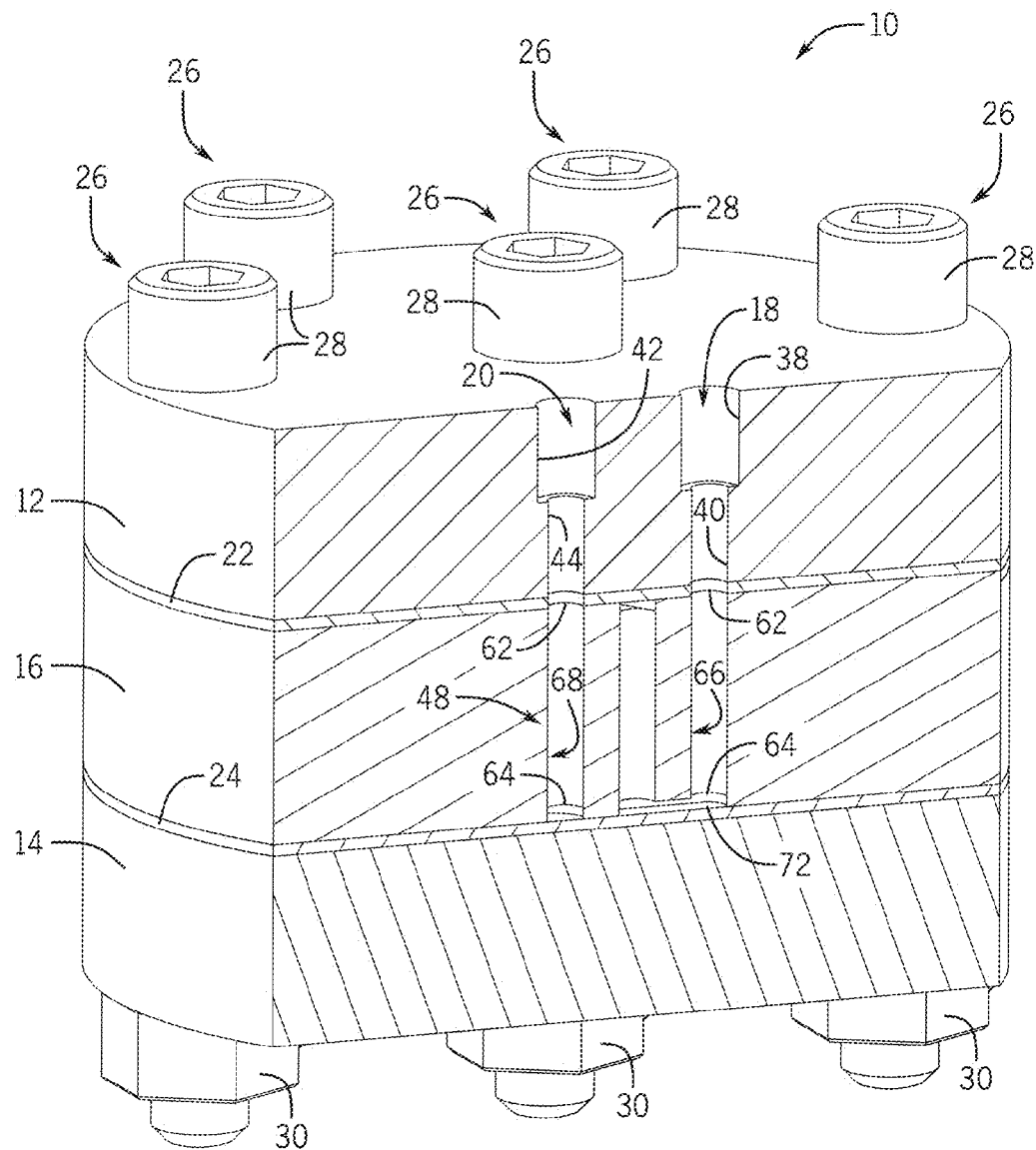
FIG. 3 shows a cross-sectional view of the phantom of FIG. 1 taken along line 3-3.

The first gasket 22 includes a first gasket inlet aperture 34 and a first gasket outlet aperture 36. The first gasket inlet aperture 34 is axially aligned with the inlet 18 of the first closing plate 12, and the first gasket outlet 36 is axially aligned with the outlet 20 of the first closing plate 12. As shown in FIG. 3, the inlet 18 defines a generally cylindrical passage in the first closing plate 12 having a first inlet passage 38 and a second inlet passage 40. The first inlet passage 38 defines a diameter which is greater than a diameter of the second inlet passage 40. In one non-limiting example, the first inlet passage 38 may include threads for receiving a fitting. In other non-limiting examples, the inlet 18 may define a generally uniform diameter and not include the first inlet passage 38 and the second inlet passage 40. The first gasket inlet aperture 34 defines a diameter which is substantially equal to the diameter of the second inlet passage 40.

Similar to the inlet 18, the outlet 20 defines a generally cylindrical passage in the first closing plate 12 having a first outlet passage 42 and a second outlet passage 44. The first outlet passage 42 defines a diameter which is greater than a diameter of the second outlet passage 44. In one non-limiting example, the first outlet passage 42 may include threads for receiving a fitting. In other non-limiting examples, the outlet 20 may define a generally uniform diameter and not include the first outlet passage 42 and the second outlet passage 44. The first gasket outlet aperture 36 defines a diameter which is substantially equal to the diameter of the second outlet passage 44.

Figure 4:
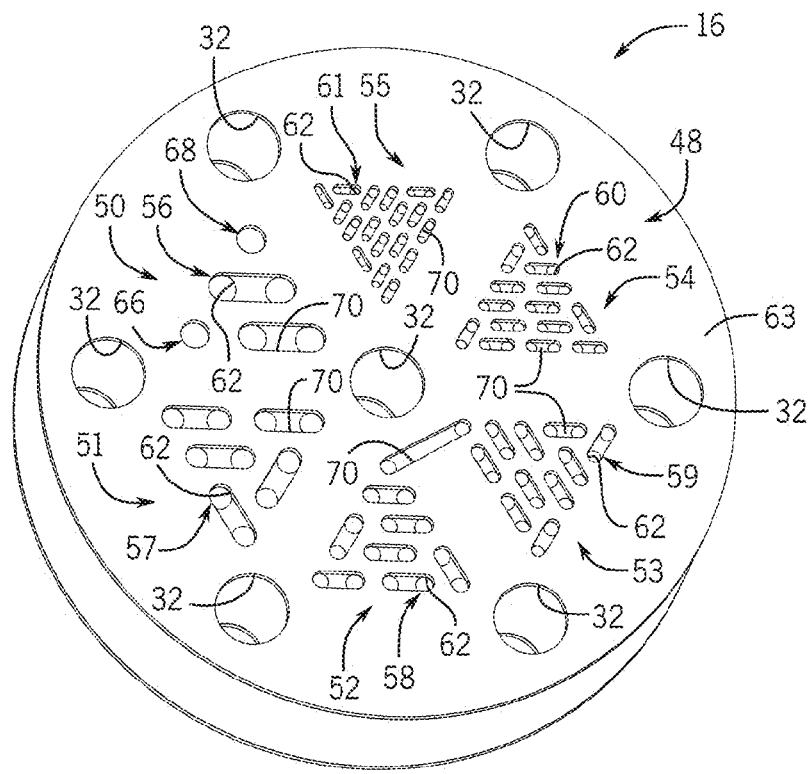
FIG. 4 shows a top-perspective view of a pattern plate of the phantom of FIG. 1.
Figure 5:
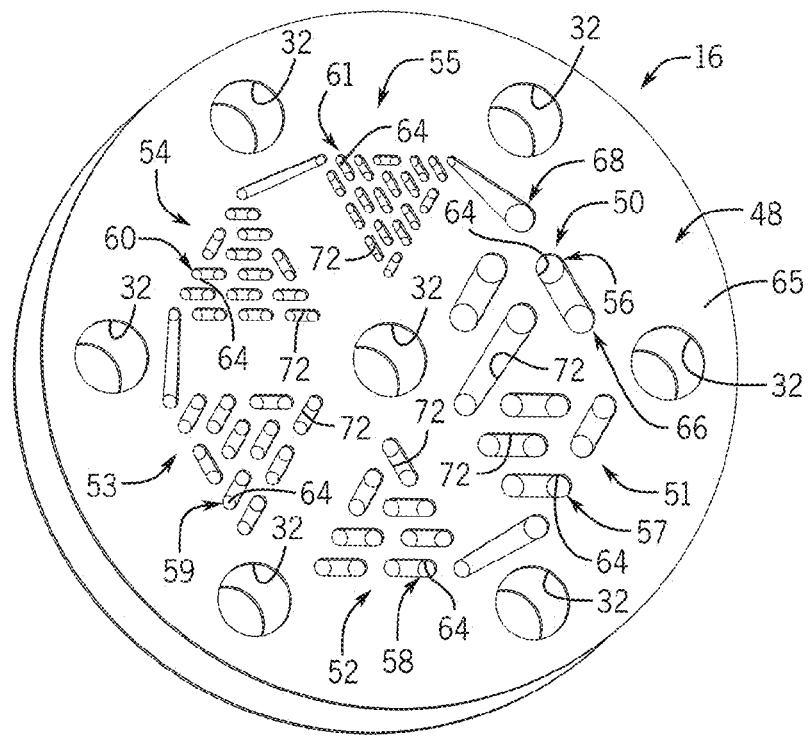
FIG. 5 shows a bottom-perspective view of a pattern plate of the phantom of FIG. 1.

With reference to FIGS. 3-5, the pattern plate 16 includes a plurality of passages 48 arranged to define a pattern for quantifying an imaging characteristic of the nuclear imagine system, as will be described in detail below. Each of the plurality of passage 48 define a generally cylindrical shape. The plurality of passages 48 are arranged into a plurality of hole pattern groups. In particular, the pattern plate 16 includes a first hole pattern group 50, a second hole pattern group 51, a third hole pattern group 52, a fourth hole pattern group 53, a fifth hole pattern group 54, and a sixth hole pattern group 55. The first hole pattern group 50 includes a first plurality of passages 56 each defining a first diameter. The second hole pattern group 51 includes a second plurality of passages 57 each defining a second diameter. The third hole pattern group 52 includes a third plurality of passages 58 each defining a third diameter. The fourth hole pattern group 53 includes a fourth plurality of passages 59 each defining a fourth diameter. The fifth hole pattern group 54 includes a fifth plurality of passages 60 each defining a fifth diameter. The sixth hole pattern group 55 includes a sixth plurality of passages 61 each defining a sixth diameter.

The first, second, third, fourth, fifth, and sixth hole pattern groups 50, 51, 52, 53, 54, and 55 are arranged circumferentially around the pattern plate 16 and each define a generally triangular shape. The first, second, third, fourth, fifth, and sixth hole pattern groups 50, 51, 52, 53, 54, and 55 combine to define a generally hexagonal shape.

Each individual passage in the first, second, third, fourth, fifth, and sixth plurality of passages 56, 57, 58, 59, 60, and 61 extend through the pattern plate 16 from a first opening 62 in a first side 63 of the pattern plate 16 to a second opening 64 in an opposing second side 65 of the pattern plate 16. As shown in FIGS. 4 and 5, the first, second third, fourth, fifth, and sixth cavity diameters are all different. The illustrated pattern plate 16 includes gradually decreasing diameters circumferentially around the pattern plate from the first hole pattern group 50 to the sixth hole pattern group 55. That is, the first diameter is greater than the second diameter, and the second diameter is greater than the third diameter, and so on (the first diameter>the second diameter>the third diameter>the fourth diameter>the fifth diameter>the sixth diameter). Additionally, each individual passage in the first, second, third, forth, fifth, and sixth plurality of passages 56, 57, 58, 59, 60, and 61 are spaced a distance equal to twice the diameter of the individual passage from neighboring passages. That is, each of the passages in the first plurality of passages 56 are spaced a distance equal to twice the first diameter from neighboring passages, and each of the passages in the second plurality of passages 57 are spaced a distance equal to twice the second diameter from neighboring passages, and so on. The above described geometric features of the pattern plate 16 enable the phantom 10 to define a Derenzo style pattern in a cross-sectional plane parallel to and between the first side 63 of the pattern plate 16 and the second side 65 of the pattern plate 16.

The first plurality of passages 50 include an inlet passage 66 and an outlet passage 68. The inlet passage 66 is axially aligned and in fluid communication with the inlet 18 of the first closing plate 12. The inlet passage 66 defines a diameter that is substantially equal to the diameter of the second inlet passage 40. The outlet passage 68 is axially aligned and in fluid communication with the outlet 20 of the first closing plate 12. The outlet passage 68 defines a diameter that is substantially equal to the diameter of the second outlet passage 44.

The pattern plate 16 includes a plurality of first side channels 70 and a plurality of second side channels 72. Each of the plurality of first side channels 70 define a channel in the first pattern plate side 62 that connect a pair of the plurality of passages 48. Each of the plurality of second side channels 72 define a channel in the second patter plate side 64 that connect another pair of the plurality of passages 48. The plurality of passages 48, the plurality of first side channels 70, and the plurality of second side channels 72 combine to define a continuous fluid flow path 74 through the pattern plate 16 that fluidly connects the inlet passage 66 to the outlet passage 68.

Figure 6:
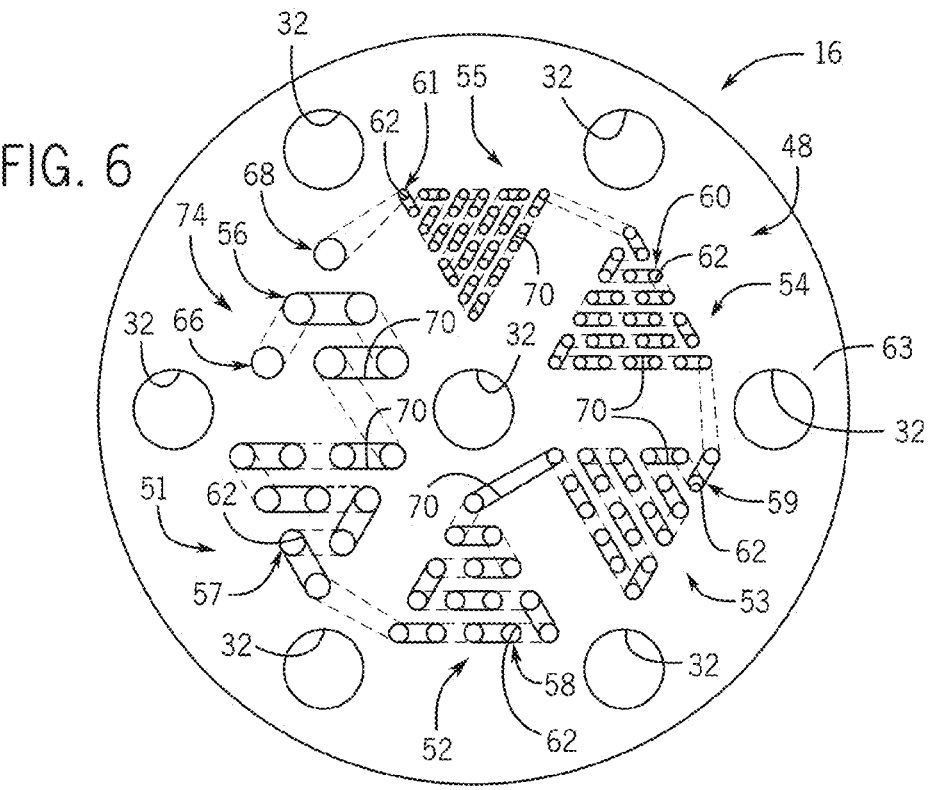
FIG. 6 shows a top view of a pattern plate of the phantom of FIG. 1 with the pattern plate transparent to illustrate a flow path of the pattern plate.
Figure 7:
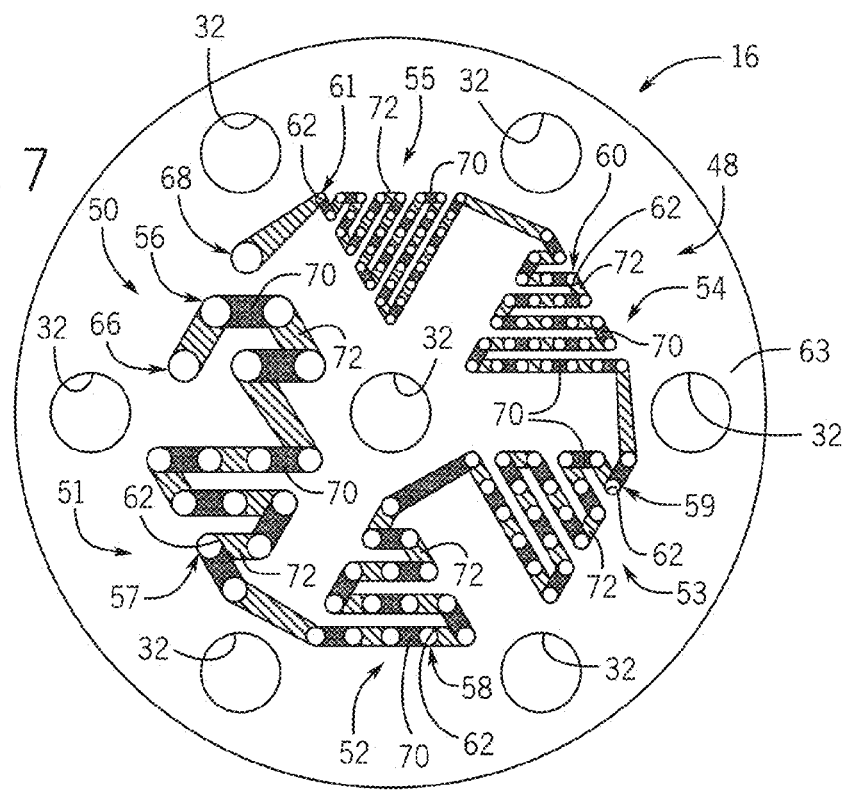
FIG. 7 shows a top view of a pattern plate of the phantom of FIG. 1 with connections between adjacent passages highlighted to illustrate which connections are made on a first side of the pattern plate and which connections are made on a second side of the pattern plate.

Turning to FIGS. 6 and 7, the continuous fluid flow path 74 through the pattern plate 16 linearly connects each of the plurality of passages 48 from the inlet passage 66 to the outlet passage 68. That is, the flow path 74 enables plurality of passages 48 to be filled sequentially and one at a time when fluid is furnished to the inlet 18. This is accomplished by connecting consecutive pairs of the plurality of passages 48 on alternating sides of the pattern plate 16 via the plurality of first side channels 70 (shown in solid in FIG. 7) and the plurality of second side channels 72 (shown in cross-hatched in FIG. 7). In particular, the pairs of the plurality of passages 48 connected by the first side channels 70 and the second side channels 72 represent a complete set of connections between the inlet passage 66 and the outlet passage 68 and are complementary. In addition, the same two of the plurality of passages 48 should not be connected on both the first side 63 of the pattern plate 16 and the second side 65 of the pattern plate 16 as this would result in a closed off flow path.

Figure 8:
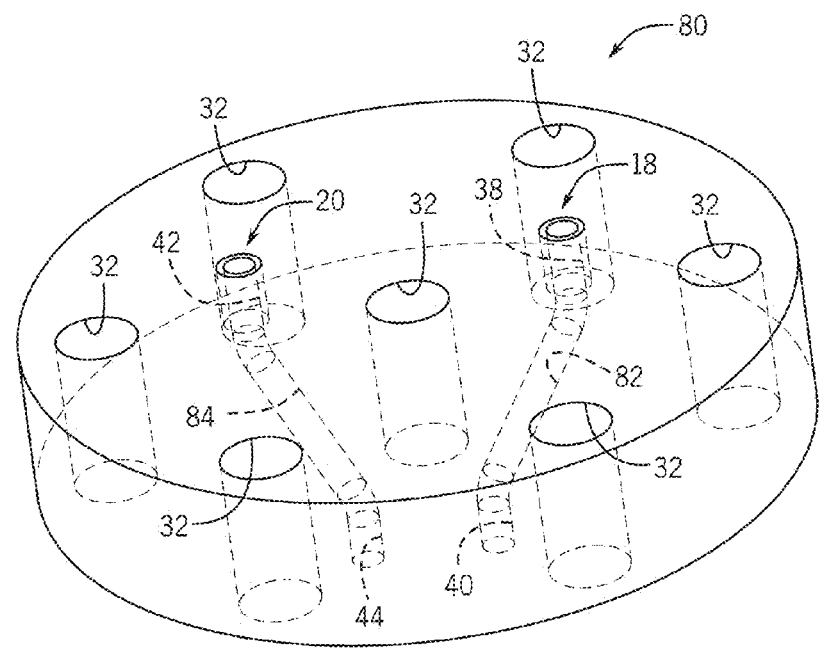
FIG. 8 shows a perspective view of a first closing plate of the phantom of FIG. 1 with the first closing plate transparent according to another embodiment of the present disclosure.

FIG. 8 shows another non-limiting example of a first closing plate 80 of the phantom 10 according to the present disclosure. The first closing plate 80 of FIG. 8 is similar to the first closing plate 12 of FIGS. 1-3 (with similar features identified with like reference numerals) except as described below or is apparent from FIG. 8. As shown in FIG. 8, the inlet 18 of the first closing plate 12 includes the first inlet passage 38, the second inlet passage 40, and an oblique inlet passage 82. Similarly, the outlet 20 of the first closing plate 12 includes the first outlet passage 42, the second outlet passage 44, and an oblique outlet passage 84. The oblique inlet passage 82 axially offsets the first inlet passage 38 and the second inlet passage 40 (and thereby the inlet passage 66), and the oblique outlet passage 84 axially offsets the first outlet passage 42 and the second outlet passage 44 (and thereby the outlet passage 68). This enables a distance between the first inlet passage 38 and the first outlet passage 42 in the first closing plate 80 to be greater than a distance between the first inlet passage 38 and the first outlet passage 42 in the first closing plate 12.

One non-limiting example of the operation of the phantom 10 will be described with reference to FIGS. 1-8. It should be know that the exemplary advantages of the phantom 10 described herein, or otherwise apparent to one of skill in the art, may be applied to other phantoms designed using the techniques and properties described herein.

In operation, the phantom 10 is used to quantify a resolution capability of the nuclear imaging system. To accomplish this, the phantom 10 is first filled with a radioisotope doped fluid. The inlet 18 of the first closing plate 12 is connected to a fluid source (e.g., a tube, a syringe, a syringe pump, etc.). A volume required to fill the continuous fluid flow path 74 with fluid can be determined either experimentally (e.g., using a predetermined volume of fluid) or theoretically (e.g., calculating the volume based on the first, second, third, fourth, fifth, and sixth diameters and a depth of the plurality of first side channels 70 and the plurality of second side channels 72). Since the volume required to fill the continuous fluid flow path 74 is known, the fluid source can provide an exact pre-determined volume of radioisotope doped fluid to the inlet 18. Once the fluid source furnishes the radioisotope fluid to the inlet 18, the fluid linearly follows the continuous fluid flow path 74 thereby filling each of the passages 48 one at a time from the inlet passage 66 to the outlet passage 68. In this way, the phantom 10 does not require any wasted or additional expensive radioisotope doped fluid to fill the plurality of passages 48. Additionally, a reduced volume required to fill the continuous fluid flow path 74 (when compared to current phantom designs) enables the phantom 10 to utilize a reduced dosage (i.e., concentration) of the radioisotope in the fluid.

Once the plurality of passages 48 are all filled with the radioisotope doped fluid, the nuclear imaging system can acquire an image of the phantom 10 along a cross-sectional plane parallel to and between the first side 63 and the second side 65 of the pattern plate 16. Because of the Derenzo style pattern defined by this cross-section, the resultant image can be used to determine the resolution capability of the nuclear imaging system.

It should be known that the pattern plate 16 of the phantom 10 may be designed to define an alternative pattern or shape to test another imaging characteristic of the nuclear imaging system. Also, the linearly fillable properties provided by the phantom 10 may be applied to patterns, shapes, or other phantoms to reduce wasted or unused radioisotope doped fluid. It should also be know that since the flow path 74 is continuous, the inlet 18 and outlet 20 are interchangeable. That is, fluid may be provided to the outlet 20 and flow to the inlet 18, if desired. Alternatively or additionally, the inlet passage 66 and the outlet passage 68 can be chosen to be any two of the plurality of passages 48, and the continuous fluid flow path 74 can be adjusted accordingly by the plurality of first side channels 70 and the plurality of second side channels 72. Alternatively or additionally, the phantom 10 can be scaled to define a desired size for the nuclear imaging system in which it is used.

EXAMPLES

Figure 9:
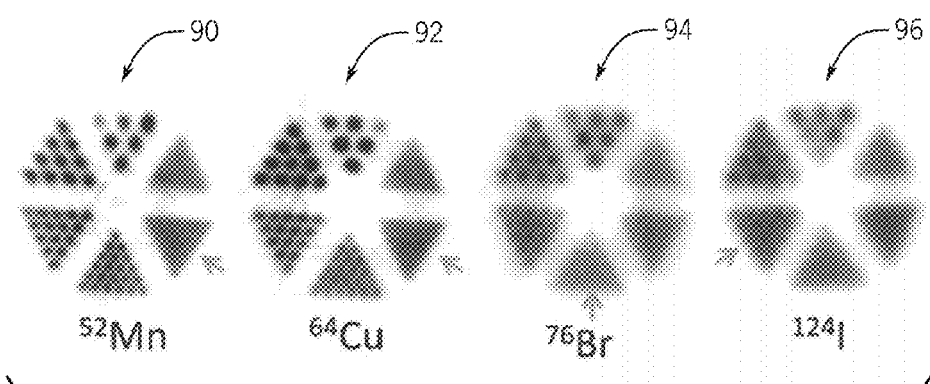
FIG. 9 shows four PET images of the phantom of FIG. 1 along a cross-sectional plane with the phantom filled with $^{52}$Mn, $^{64}$Cu, $^{76}$Br, and $^{124}$I.

The phantom 10 was imaged along the cross-section plane parallel to and between the first side 63 and the second side 65 of the pattern plate 16. The phantom 10 was imaged using a UWCCC Siemens Inveon MicroPET/CT scanner with the continuous fluid flow path 74 of the phantom 10 filled using four different radioisotopes (i.e., $^{52}$Mn, $^{64}$Cu, $^{76}$Br, $^{124}$I) doped into water. The resultant images are shown in FIG. 9. Image 90 of FIG. 9 was acquired with the continuous fluid flow path 74 of the phantom 10 filled with $^{52}$Mn, image 92 of FIG. 9 was acquired with the continuous fluid flow path 74 of the phantom 10 filled with $^{64}$Cu, image 94 of FIG. 9 was acquired with the continuous fluid flow path 74 of the phantom 10 filled with $^{76}$Br, and image 96 of FIG. 9 was acquired with the continuous fluid flow path 74 of the phantom 10 filled with $^{124}$I. As shown by images 90, 92, 94, and 96 of FIG. 9, the phantom 10 successfully provides a Derenzo style pattern for the MicroPET/CT scanner to image, and determine a resolution capability of the MicroPET/CT scanner for the four different radioisotopes.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A phantom for a nuclear imaging system, the phantom comprising:
    a pattern plate including a plurality of passages each extending through the pattern plate from a first opening on a first side of the pattern plate to a second opening on an opposing second side of the pattern plate; and
    a plurality of channels arranged on the first side of the pattern plate and the second side of the pattern plate to sequentially interconnect each of the plurality of passages thereby forming a continuous fluid flow path from an inlet passage of the pattern plate to an outlet passage of the pattern plate.

2. The phantom of claim 1, further comprising a first closing plate and a second closing plate compressing the pattern plate therebetween.

3. The phantom of claim 2, wherein the first closing plate includes an inlet in fluid communication with the inlet passage of the pattern plate and the first closing plate includes an outlet in fluid communication with the outlet passage of the pattern plate.

4. The phantom of claim 3, wherein the first closing plate further includes an oblique inlet passage axially offsetting the inlet from the inlet passage of the pattern plate and includes an oblique outlet passage axially offsetting the outlet from the outlet passage of the pattern plate.

5. The phantom of claim 2, further comprising a first gasket arranged between the first closing plate and the pattern plate and a second gasket arranged between the second closing plate and the pattern plate.

6. The phantom of claim 5, wherein the first gasket includes a first gasket inlet aperture axially aligned with the primary inlet passage and a first gasket outlet aperture axially aligned with the final outlet passage.

7. The phantom of claim 1, wherein the plurality of channels include a plurality of first side channels and a plurality of second side channels, the plurality of first side channels each defining a channel in the first side of the pattern plate that connect a pair of the plurality of passages, and the plurality of second side channels each defining a channel in the second side of the pattern plate that connect another pair of the plurality of passages.

8. The phantom of claim 7, wherein consecutive pairs of the plurality of passages connected by the continuous flow path are alternatingly connected by one of the plurality of first side channels and one of the plurality of second side channels.

9. The phantom of claim 1, wherein the plurality of passages are arranged into a plurality of hole pattern groups.

10. The phantom of claim 9, wherein the plurality of hole pattern groups are arranged circumferentially around the pattern plate.

11. The phantom of claim 9, wherein each of the hole pattern groups define a generally triangular shape.

12. The phantom of claim 9, wherein plurality of hole pattern groups combine to define a generally hexagonal shape.

13. The phantom of claim 9, wherein plurality of hole pattern groups include a first hole pattern group formed by a first plurality of passages each having a first diameter, a second hole pattern group formed by a second plurality of passages having a second diameter, a third hole pattern group formed by a third plurality of passages having a third diameter, a fourth hole pattern group formed by a fourth plurality of passage each having a fourth diameter, a fifth hole pattern group formed by a fifth plurality of passages each having a fifth diameter, and a sixth hole pattern group formed by a sixth plurality of passages having a sixth diameter.

14. The phantom of claim 13, wherein the first diameter, the second diameter, the third diameter, the fourth diameter, the fifth diameter, and the sixth diameter are all different.

15. The phantom of claim 13, wherein the first diameter is greater than the second diameter, the second diameter is greater than the third diameter, the third diameter is greater than the fourth diameter, the fourth diameter is greater than the fifth diameter, and the fifth diameter is greater than the sixth diameter.

16. The phantom of claim 13, wherein each of the first plurality of passages are spaced apart a distance equal to twice the first diameter, each of the second plurality of passages are spaced apart a distance equal to twice the second diameter, each of the third plurality of passages are spaced apart a distance equal to twice the third diameter, each of the fourth plurality of passages are spaced apart a distance equal to twice the fourth diameter, each of the fifth plurality of passages are spaced apart a distance equal to twice the fifth diameter, and each of the sixth plurality of passages are spaced apart a distance equal to twice the sixth diameter.

17. The phantom of claim 1, wherein the plurality of passages are cylindrically shaped.

18. The phantom of claim 1, wherein the plurality of passages in the pattern plate define a Derenzo-style pattern in a cross-sectional plane parallel to and between the first side of the pattern plate and the second side of the pattern plate.

19. A phantom for a nuclear imaging system, the phantom comprising:
a pattern plate including a plurality of passages each extending through the pattern plate from a first opening on a first side of the pattern plate to a second opening on an opposing second side of the pattern plate; and
a plurality of continuous fluid flow paths arranged on the first side of the pattern plate and the second side of the pattern plate to sequentially interconnect each of the plurality of passages from an inlet passage of the pattern plate to an outlet passage of the pattern plate.

20. A method of determining an imaging characteristic of a nuclear imaging system using a phantom fillable with a radioisotope doped fluid, the phantom including a pattern plate and a continuous fluid flow path, the pattern plate including a plurality of passages arranged in a calibration pattern, the plurality of passages including an inlet passage and an outlet passage, the continuous fluid flow path sequentially interconnecting each of the plurality of passages from the inlet passage to the outlet passage, the method comprising:
furnishing the radioisotope doped fluid to the inlet passage of the pattern plate;
filling the plurality of passages in the pattern plate, via the continuous fluid flow path, with a pre-determined volume of the radioisotope doped fluid;
upon filling the plurality of passages with the pre-determined volume of radioisotope-doped fluid, imaging, with the nuclear imaging system, a cross-section of the pattern plate which defines the calibration pattern; and
upon imaging the cross-section of the pattern plate which defines the calibration pattern, determining the imaging characteristic of the nuclear imaging system.

\* \* \* \* \*